(12) United States Patent
Post et al.

(10) Patent No.: US 6,211,799 B1
(45) Date of Patent: Apr. 3, 2001

(54) METHOD AND APPARATUS FOR TRANSBODY TRANSMISSION OF POWER AND INFORMATION

(75) Inventors: E. Rehmi Post, Cambridge; Babak Nivi, Boston; Neil Gershenfeld, Somerville, all of MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 08/965,465

(22) Filed: Nov. 6, 1997

(51) Int. Cl.[7] .................................................. H03K 17/94
(52) U.S. Cl. .................. 341/33; 340/10.51; 340/870.37; 345/156; 455/100
(58) Field of Search .................................. 341/33, 32, 34; 345/156; 455/100, 90, 127; 708/132, 141, 143; 340/825.22, 825.27, 10.51, 870.3, 870.37

(56) References Cited

U.S. PATENT DOCUMENTS

| | | | |
|---|---|---|---|
| 4,069,659 | * 1/1978 | Harris et al. | 708/143 |
| 5,204,672 | 4/1993 | Brooks | 340/825 |
| 5,796,827 | * 8/1998 | Coppersmith et al. | 308/9 |
| 5,874,725 | * 2/1999 | Yamaguchi | 340/825.34 |
| 5,914,701 | * 6/1999 | Gersheneld et al. | 455/100 |
| 5,953,425 | * 9/1999 | Selker | 380/25 |

FOREIGN PATENT DOCUMENTS 2 129 176   5/1984 (GB) ............................ G07C/11/00

OTHER PUBLICATIONS

Zimmerman, *Personal Area Networks (PAN): Near–Field Intra–Body Communication*, MIT Thesis (1995). p. 1–81.

* cited by examiner

Primary Examiner—Michael Horabik
Assistant Examiner—Timothy Edwards, Jr.
(74) Attorney, Agent, or Firm—Testa, Hurwitz & Thibeault LLP

(57) ABSTRACT

Capacitive coupling is used to transmit data and power through a user's body. In one implementation, a transmitter carried by the user transmits power and data to a receiver, which is also carried on the user's body. The signal that the transmitter applies to the user's body not only contains a data component, but also powers the receiver and enables it to detect and decode the data. In other implementations, the transmitter or the receiver is physically displaced from the user's body (although both receiver and transmitter are coupled to environmental ground), and data and power are transmitted when the transmitter and receiver become sufficiently proximate—via the user's body—to permit capacitive coupling. The disclosed approach is amenable to a wide variety of applications, ranging from "interbody" exchange of digital information between individuals through physical contact (e.g., a handshake) to "intrabody" data transfer (e.g., between a paging device worn in the shoe and a wristwatch display device) to devices that permit communication between the user and his or her immediate environment.

12 Claims, 3 Drawing Sheets

METHOD AND APPARATUS FOR TRANSBODY TRANSMISSION OF POWER AND INFORMATION

FIELD OF THE INVENTION

The present invention relates to electronic communication, and in particular to the propagation of electrical signals across a user's body through electrostatic coupling.

BACKGROUND OF THE INVENTION

The goal of truly integrating computational capacity with the everyday lives of individuals has consumed substantial research effort, and from a variety of perspectives. Through component miniaturization, wearable items (such as wristwatches, jewelry, and clothing accessories) can now offer computer processing power to perform a variety of tasks while remaining casually and continuously available. Recent advances in fabric design permit clothing itself to carry electrical signals, while electrodes distributed around a an individual's environment can silently and unobtrusively monitor position, orientation and movements. In these ways, processing capacity can be dispersed over various worn components, and the user can, without conscious effort, interact computationally with the surrounding environment.

An important principle of design for wearable devices is adaptation to users' existing habits and preferences, rather than forcing the user to adapt to accommodate new appliances. The concept of "personal area networks" (PANs), which utilize the user's body as an electronic communication channel, represents a significant step in this direction. As described in U.S. Pat. No. 5,914,701, electrostatic coupling among worn or carried electronic devices allows these items to intercommunicate via the user's body, sharing data or control signals among themselves, or transferring data to an external recipient (such as another person or a wall-mounted receiver) by close proximity or touching.

Electrostatic coupling represents a departure from traditional forms of electronic communication, which involve radiated energy. For example, radio-frequency identification (RFID) devices have been employed for some time to remotely sense parameters of interest in people or objects. An RFID device receives a wireless signal from an externally located "reader," which determines the parameter of interest based on the response of the RFID device to the transmitted signal. A simple application of this technology is security: an individual wears an RFID "tag" or badge, and a controlled-entry system unlocks a door only if the wearer's tag is recognized as s/he approaches.

Radiative systems can be configured for a relatively large (i.e., far field) read range. But this capability can actually represent a disadvantage if the environment contains multiple, independent RFID devices, since the reader will excite all devices within the read range simultaneously. Proximately located devices, in other words, cannot share the same frequency channel; separate addressing requires separate frequencies or cumbersome efforts to focus the electromagnetic field from the reader.

Magnetostatic and electrostatic RFID systems, by contrast, operate through near-field interaction, and thereby facilitate selective coupling or "channel sharing"; that is, so long as the tagged items are not immediately adjacent (i.e., within a few centimeters of each other), they can be individually addressed. In terms of selectivity, electrostatic systems offer practical advantages in terms of the ease of focusing an electric field as compared with a magnetic field.

Electrostatic systems also offer manufacturing and cost advantages, since the induction coil required for magnetostatic systems is eliminated and electrodes can be conveniently and inexpensively deposited on substrates of widely varying shapes and materials. For example, the tag in a magnetostatic system may have a coil with 100–1000 turns and a radius of 1–5 cm, while a typical reader has a 20-cm coil.

On the other hand, a person's body can act as a shield in electrostatic systems, compromising the coupling between reader and RFID device. The PAN approach, which uses the entire body as a signal carrier, not only overcomes this limitation, but also substantially extends the read range. For example, a computer housed in a user's shoe can readily communicate electrostatically with the user's wristwatch, personal digital assistant, and/or notebook computer.

One limitation of the PAN concept has been the need for autonomously powered devices. Again, components such as batteries or power supplies add significantly to the weight and cost of PAN devices, and contradict the goal of seamless integration of computational capacity into the user's lifestyle and habits.

DESCRIPTION OF THE INVENTION

BRIEF SUMMARY OF THE INVENTION

The present invention capacitively transmits not only data but power through a user's body. In one implementation, a transmitter carried by the user transmits power and data to a receiver, which is also carried on the user's body; the return path for the current is provided by environmental ground. The signal that the transmitter applies to the user's body not only contains a data component, but also powers the receiver and enables it to detect and decode the data.

Various strategies for simultaneous transmission of power and data may be employed. In one approach, power and data are simply transmitted at different frequencies. In another approach, the data is transmitted by modulating a carrier from which power is derived. Virtually any modulation scheme can be adapted to the present invention. For example, data may be encoded by frequency modulation of a carrier; the receiver recovers the data by detecting carrier modulations, and derives power from the frequency-varying carrier itself. Alternatively, the data may be encoded by amplitude modulation or phase modulation of a carrier. In still another approach, the data is modulated using, for example, a pseudorandom code to provide spread-spectrum encoding within a broadband carrier, with the carrier again supplying power. And in yet another approach, the data is not actually "transmitted" at all, but is instead imparted to the transmitter by the receiver in the form of loading variations. In the time domain, the temporal pattern of these variations can encode a sequence of bits. In the frequency domain, multiple receivers resonating at different frequencies can impart information merely by their presence or absence, or can instead impart a continuous range of information through variation of resonant frequency (or frequencies).

Furthermore, the coupling of resonators to a transmitter (i.e., a reader) can impart information about their proximity to the transmitter. The coupling strength is inversely proportional to the square of the distance between transmitter and receiver. Receivers having different resonant frequencies can be individually addressed and the coupling strengths separately assessed to obtain distance measurements. Increasing the number of resonators increases the resolution of the measurement (if they lie in a straight line) and the dimensionality of the measurement (if they are not collinear).

In other implementations, the transmitter or the receiver is physically displaced from the user's body (although both receiver and transmitter are coupled to environmental ground), and data and power are transmitted when the transmitter and receiver become sufficiently proximate—via the user's body—to permit capacitive coupling. For example, the transmitter may refrain from sending the data component until alerted (e.g., via a loading measurement) of the coupling to a receiver. In still other implementations, the user may wear more than one receiver. The receivers may also be capable of transmitting data to other receivers. Modulation schemes such as spread-spectrum FM, time-division multiplexing or frequency-division multiplexing facilitate simultaneous operation of multiple transmitters, each using a different modulation parameter.

The invention is amenable to a wide variety of applications, ranging from "interbody" exchange of digital information between individuals through physical contact (e.g., a handshake) to "intrabody" data transfer (e.g., between a paging device worn in the shoe and a wristwatch display device) to devices that permit communication between the user and his or her immediate environment. An important example of the latter category relates to the use of wearable electrostatic devices for security or other purposes. An external reader (i.e., transmitter) may detect data from the tag through loading variations or by reception of a return signal; alternatively, the reader may be carried by the user to identify or discriminate among multiple tagged items (e.g., to determine the tagged contents of boxes in a warehouse).

This approach has both cost and weight advantages over conventional RFID. As noted previously, far-field or magnetostatic devices require antennas to transmit or receive radiated magnetic flux. By contrast, because it operates electrostatically, the present invention may utilize small (compared to a wavelength) and arbitrarily shaped electrodes, and no flux-coupling coil is necessary.

And once again, by using the body as a medium for signal propagation—i.e., as part of the circuit—the present invention extends the effective range of operation substantially beyond the free-space (i.e., unassisted) coupling distance. For example, a signal may readily travel from a floormat to an RFID tag carried in the user's pocket or worn on the user's head—a distance many times that of the free-space coupling range. Indeed, the small coupling distance associated with electrostatic devices is frequently beneficial. In an environment with many RFID-tagged items (such as a warehouse), a system utilizing broadcast energy may couple to numerous tags in the immediate environment; coupling in an electrostatic system, on the other hand, may be confined to particular chosen items without risk of incidental coupling to other tagged items.

Generally in accordance with the invention, the transmitter and receiver are coupled through a user and room ground. The human body acts as a good conductor capacitively coupling receiver and transmitter. The transmitter, however, produces low-frequency (generally 100 kHz to 10 MHz) AC signals that pass, through capacitive coupling, as displacement currents into and from the body of the user, carrying both power and data. Since the transmitter and receiver do not couple with one another directly, the shared room ground provides the return path for the current.

At low frequencies, the human body behaves as a capacitive load with minimal radiation of RF energy. Operation of the invention, therefore, is largely immune to eavesdropping and interference, and does not fall within government regulations directed toward radiative systems. A transmitter in accordance with the invention may include a signal generator and a pair of electrodes, sometimes referred to as "inner" (i.e., closer to the user's body) and "outer" electrodes. The signal generator produces modulated signals that vary the voltage between the electrodes. The inner electrode is closely coupled capacitively to the user's body such that the "quasi-electrostatic" field resulting from the electrode potential causes a displacement current to pass to user's body. The outer electrode is oriented so that its coupling to the room ground is stronger than that of the inner electrode. In environmental coupling applications, by contrast, the grounding electrode may be directly connected to room ground.

The receiver may include a pair of electrodes, rectification circuitry to convert the power component of the transmitted signal into usable DC, and a detector/demodulator that obtains the data component of the transmitted signal. One of the electrodes is closely coupled capacitively to the user's body so as to receive displacement current passing through the body. The current entering the receiving electrode passes through the rectification and detector circuitry and thereafter to the other electrode, which is asymmetrically coupled capacitively to room ground to complete the circuit path. Due to this asymmetric coupling, a potential difference exists across the electrodes.

Receivers in accordance with the invention generally involve active circuitry that draws power from the transmitted signal in order to support operation. As noted above, however, in some embodiments the receiver circuitry is passive, imparting data through modulation of an electrical characteristic that is sensed by the transmitter.

BRIEF DESCRIPTION OF THE DRAWINGS

The foregoing discussion will be understood more readily from the following detailed description of the invention, when taken in conjunction with the accompanying drawings, in which.

DETAILED DESCRIPTION OF THE PREFERRED EMBODIMENTS

Figure 1:
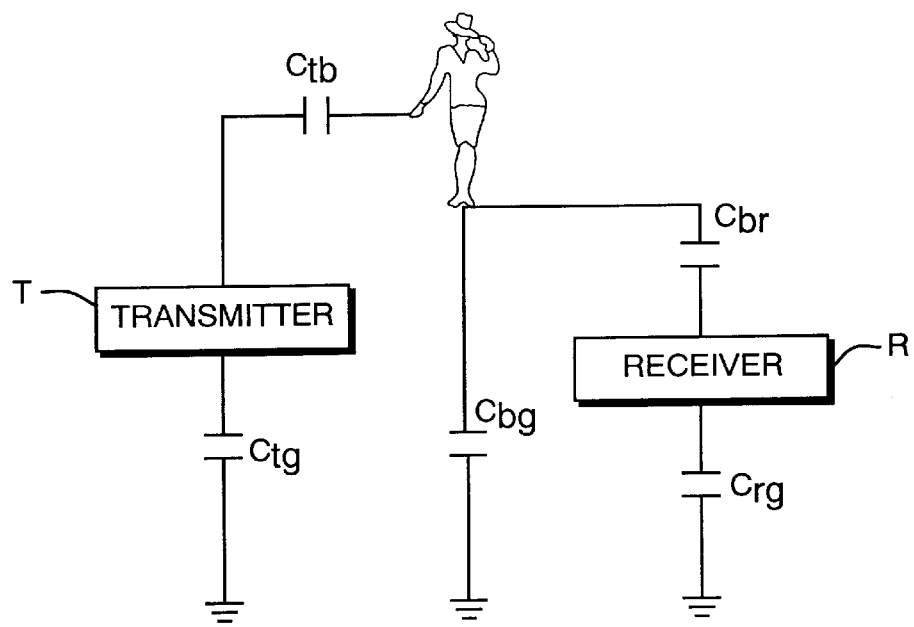
FIG. 1 schematically represents a communication system in accordance with the present invention.

FIG. 1 is a generalized representation of intra-body and inter-body power and data transmission in accordance with the present invention, reflecting capacitive coupling of displacement current into the body and the use of the environment as the current return path. The schematic arrangement shown in FIG. 1 is valid for both intrabody and interbody modes of capacitive coupling. In the figure, a transmitter T applies an AC signal $V_t$ to the body of a user P via capacitive coupling, represented as a capacitance $C_{tb}$. This signal passes through the user's body to a receiver R, also via a capacitive electrostatic linkage, which is indicated at $C_{br}$.

The transmitter T, person P, and receiver R are all capacitively coupled to the ambient ground, as indicated by the capacitances $C_{tg}$, $C_{bg}$, and $C_{rg}$, respectively. (As noted below, systems using an external or environmental transmitter can be connected directly to ground.) These capacitances can be a combination of air and earth ground, and materials in the vicinity of person P (such as plumbing, metal cabinets, reinforcement studs, etc.) can contribute to $C_{bg}$ and $C_{rg}$. Generally, the noted capacitances are on the order of 10–100 pF. Not shown in the figure are various parasitic capacitances. These are usually negligible but, depending on the configuration, can interfere with operation. Although minimizing them for a given implementation is well within the skill of those in the art, a more detailed treatment of the electrostatic model, including parasitic capacitances, may be found in Zimmerman, "Personal area networks: near-field intrabody communication," *IBM Systems Journal* 35(3):609–617 (1996).

In an interbody coupling configuration, the transmitter T is physically displaced from the person P. For example, in a controlled-entry security system, the transmitter T may be connected to an electrode mounted on a doorjamb, or to the doorknob itself (which serves as an electrode). The user P becomes electrostatically coupled to the transmitter electrode as s/he approaches, with the magnitude of $C_{tb}$ reaching adequate levels for coupling only when the user (or his or her appendage) approaches very closely. Accordingly, without the human body as an electrostatic conduit, capacitive coupling between the transmitter and receiver would be negligible unless brought within centimeters of each other. The body effectively extends the coupling range to meters. The transmitter T may be connected to ground (rather than coupling environmentally, thereby eliminating—or at least substantially reducing—$C_{tg}$).

In the case of intrabody coupling, both transmitter and receiver elements, as well as the user, couple environmentally to ambient ground. Generally, the transmitter T will be provided with a source of power, with the receiver R drawing power from the current applied to the body by the transmitter (i.e, via the capacitances $C_{tb}$ and $C_{br}$). The transmitter T may be powered by a conventional voltage source (e.g., a battery), but this approach adds weight and cost to an implementation otherwise amenable to unnoticeable integration into the user's clothing. Consequently, the transmitter T is more desirably powered by means for parasitically drawing mechanical energy from the user's movements and transducing this into electrical power. As described in Zimmerman, supra, for example, it is possible to locate a piezoceramic pile in the user's shoe, the user's gait repeatedly flexing and extending the piezo material to produce electrical power, which charges a capacitor. It has been found that despite the body's electrical impedance, the power generated in this manner and applied to the receiver via the user's body is sufficient to drive its electrical circuitry.

In one approach to exchange of data between a body-borne receiver and a transmitter that may also be worn (but is, more typically, located externally), the receiver varies with time the load that it presents to the transmitter. Thus, in this time-domain "loading mode" of operation, the receiver effectively sends bits of information to the transmitter by modulating the Thévenin equivalent load to which the transmitter is coupled. Generally, $V_1 = V_0 e^{j\omega_1 t}$ where $\omega_1 = 2\pi f_t$ and $V_0 \approx 50\text{--}1000$ V. At 50 V, for example, approximately 1.5 milliwatt of power is available to the receiver.

In a variation to this approach, the transmitter—configured as a transceiver—excites the resonator using a narrow or broadband signal. The transmitter then ceases transmission and detects the ringdown of the stored energy that was imparted to the resonator by the excitation signal. Thus, instead of detecting an intrinsic characteristic of the receiver such as impedance, this approach measures the oscillatory decay of energy in the receiver that produces a characteristic frequency response (based on the values of the resonator components).

Figure 2:
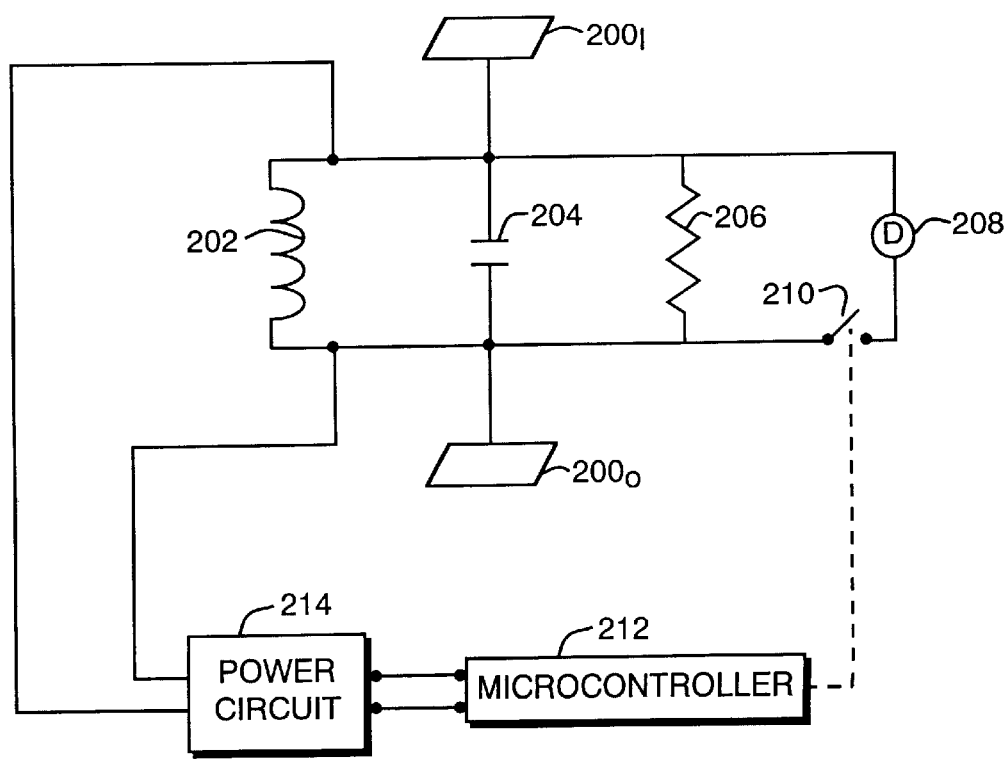
FIG. 2 schematically represents a "loading-mode" receiver.

FIG. 2 illustrates an exemplary receiver which, in its simplest realization, is incapable of varying its impedance and can therefore "transmit" only a single bit—identifying itself, that is, to a transmitter applying a time-varying voltage at the receiver circuit's resonant frequency through the change in presented impedance and, hence, the resulting change in transmitter output current. It is by no means obvious that small perturbations in impedance (or, for that matter, the presence and decay of energy stored in a resonant structure) can be reliably detected through the body, as facilitated by the present invention.

The basic receiver is an LRC circuit, comprising a pair of electrodes $200_I$, $200_O$, referred to individually as an inner electrode $200_I$ and an outer electrode $200_O$; an inductance 202, which may be a lumped-element or discrete device, but need not be a wound coil (as would be necessary in a magnetically coupled system); and a capacitance 204; and a resistance 206. It has been found that the element 202 can be eliminated as a practical matter. The electrodes $200_O$, $200_I$ are capacitively and asymmetrically coupled to the room ground (via $C_{rg}$) and to the user (via $C_{br}$), respectively. Typically, the receiver is worn such that electrode $200_I$ is directly adjacent to or in contact with a portion of the user's body, while electrode $200_O$ is presented to the external environment.

Even a "single-bit" receiver such as that described above has numerous practical uses. Because the loading peak occurs at a specific resonant frequency, that frequency—determined by the values selected for the components 202, 204—may be used to identify the receiver. Thus, a security system can include a transmitter applying a time-varying voltage at a predetermined frequency to a doorknob. If the user is carrying a receiver whose resonant frequency matches the transmitter output, the transmitter will detect a loading peak through the user's body when s/he approaches or touches the doorknob; if not, the baseline loading level indicates a mismatch. Indeed, because the receiver can be made very small and light, the user can wear a number of these, each having a different resonant frequency and representing a separate bit. A transmitter T can be equipped with sweep circuitry enabling it to apply the AC signal at a stepped or continuous sequence of frequencies, electrostatically detecting loading peaks and, therefore, the presence of particular receivers—i.e., bits in the frequency domain—on the person P. In other words, one can define a series of resonant frequencies, each corresponding to a bit, and the presence or absence of a receiver at each such frequency indicates the binary state of the corresponding bit. The higher the quality factor (Q) of the receivers' resonators, the easier they will be to detect, and the more closely they may be spaced in frequency.

More generally, however, it is convenient for the receiver to be able to change, over time, its electrical characteristics in a manner detectable by the transmitter. By selectably altering its response to received electrical energy, the receiver can effectively convey—that is, "transmit"—information. One application of this approach facilitates detection of continuous characteristics. As disclosed in U.S. Pat. No. 6,025,725 the entire disclosure of which is hereby incorporated by reference, the capacitor of a resonator may contain a dielectric material whose electrical properties alter in response to changes in an external condition, such as temperature, humidity, light, or the magnitude of an applied force. The capacitor may, for example, contain as a dielectric a sheet of polyvinylidene difluoride (PVDF), which exhibits both piezoelectric and pyroelectric properties. The resonant frequency of a receiver containing such a resonator, therefore, will change in continuous, quantitative response to the external condition, so that by detecting the value of the resonant frequency (using, for example, a sweep generator in the transmitter), a transmitter electrostatically coupled to the receiver can thereby sense that condition.

Alternatively, modulation of the receiver's response can be used to convey a series of bits in the time domain. To accomplish this, an additional component or device 208 is alternately connected and disconnected to the circuit by means of a switch 210. The result of connecting device 208 is a change in the impedance of the receiver, which is sensed by the transmitter as a change in loading; repeated changes in loading in accordance with a pattern representing information is, in effect, amplitude modulation. If desired (e.g., for better noise immunity), the AM carrier can itself contain a subcarrier encoding another modulated signal. For example, the AM carrier can be demodulated into a square wave of varying pulse widths, the variations representing an FM encoding of data.

If device 208 is a parasitic resistor or a pair of clamping diodes, connection of device 208 alters the Q of the receiver circuit; if device 208 is a capacitor or inductor, the resonant frequency is altered. Changing the Q of the receiver is herein referred to as "Q-switching," while changing the resonant frequency is called "frequency shift keying" (FSK).

Q-switching or FSK, of course, requires active circuitry. In one implementation, the circuit comprises a microcontroller chip or circuit 212, which is connected to switch 210 and is configured to open and close the switch in a temporal pattern corresponding to a stream of binary data. Microcontroller 212 draws power from a power circuit, which is itself connected to the LRC circuit so as to draw power from a signal transmitted electrostatically to electrodes $200_I$, $200_O$. Power circuit 214 comprises rectification circuitry and a charging capacitor, maintaining a relatively constant DC output notwithstanding variations in the electrical energy of the LRC circuit caused by operation of switch 210 (i.e., "transmission" of bits). Because the power applied to microcontroller 212 is relatively constant, it simply becomes part of the baseline loading level of the overall circuit.

In an exemplary embodiment, the receiver comprises a discrete 9.5 mH inductor, an RFID chip (e.g., the V4050 chip supplied by EM Microelectronic-Marin SA, although the choice of RFID chip is not critical), and the two electrodes. The V4050 chip is a 2-pin device that can be operated to transmit stored data by Q-switching. It contains an integrated 170 pF capacitor (i.e., the capacitance 204), so the receiver is resonant at 125 kHz, as well as suitable rectification circuitry. The chip also contains an electronically erasable read-only memory of 1 kbit that can be programmed by the transmitter (i.e., by capacitively coupling to the chip through the user's body), and performs Q-switching in accordance with the binary pattern stored in its memory. As noted earlier, the inductor may be removed without catastrophic effects on the the read range or the rate of data-transmission errors. In the present context, "read range" means the maximum distance between the user's body (or appendage) and the transmitter electrode, usually on the order of centimeters.

Figure 3:
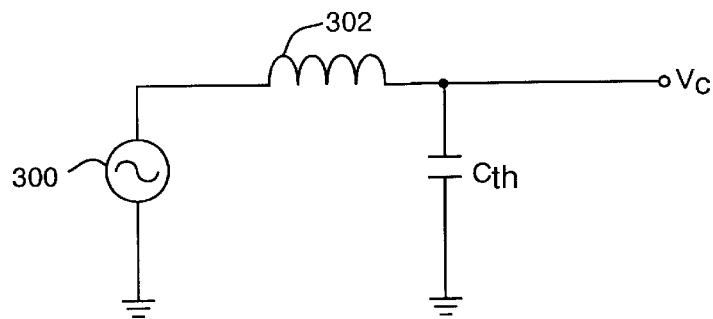
FIG. 3 schematically represents an equivalent loading-mode transmitter circuit.

The manner in which data is read from the receiver by the transmitter may be understood as follows. At the receiver's resonant frequency, the load experienced by the transmitter is mainly capacitive. Accordingly, the phase of the Thévenin equivalent impedance $Z_{th}$ seen by the transmitter is approximately $-\pi/2$, and $Z_{th}$ may be represented as $Z_{th}=1/j\omega C_{th}$, where $C_{th}$ is a real number and represents the Thévenin equivalent capacitance. Under this assumption, only the value of $C_{th}$ changes as a consequence of Q-switching or FSK (that is, the phase of $Z_{th}$ remains at $-\pi/2$). As a result, detecting the bits "transmitted" by the receiver amounts to measuring a digitally modulated capacitance $C_{th}$. This may be accomplished using the generalized transmitter circuit shown in FIG. 3. The circuit comprises an AC voltage source 300 and an inductor 302, connected such that $C_{th}$ becomes part of a series LC tank circuit; in other words, the inductor 302 is capacitively coupled to the user via an electrode (indicated by the connection to $C_{th}$), the user wearing the receiver in which $C_{th}$ originates. $V_c$, of course, corresponds to the voltage across $C_{th}$. Voltage source 300 is driven at the resonant frequency of the tank circuit. That is, with the Q-switching or FSK circuitry in the state corresponding to a zero bit, a baseline value $C_0$ for $C_{th}$ is calculated, and voltage source 300 is driven at $\omega_r=1/\sqrt{LC_0}$ (where L is the value of inductor 302). When the receiver circuitry is operated to change states to a one bit (i.e., $C_{th}$ changes from $C_0$ to a different value $C_1$), the transmitter senses this by detecting a change in the amplitude or phase of $V_C$. Alternatively, the transmitter may be designed to detect a change in the resonant frequency from $\omega_r=1/\sqrt{LC_0}$ to $\omega_r=1/\sqrt{LC_1}$. The basic transmitter circuitry itself can take a variety of forms based on the general approach shown in FIG. 3. For example, the transmitter may contain a Tesla coil with suitable tuning feedback circuitry to increase the transmitted voltage and data sensitivity.

Figure 4:
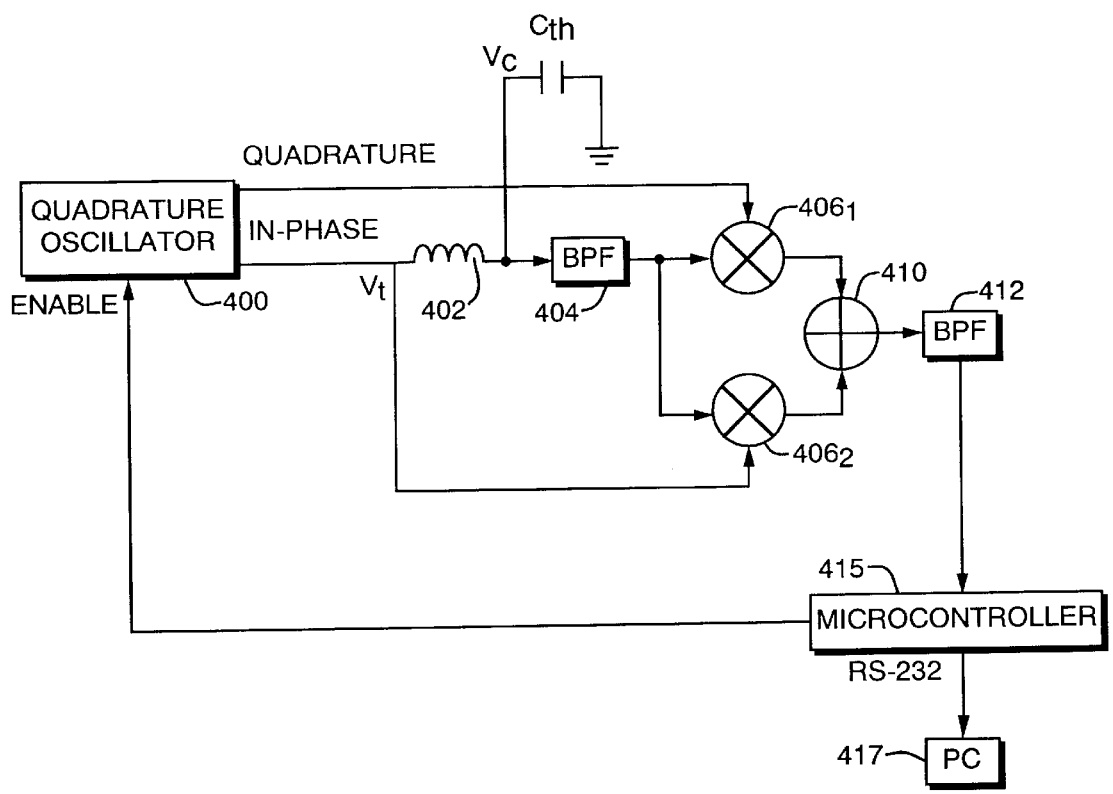
FIG. 4 schematically illustrates a loading-mode transmitter in greater detail.

In effect, Q-switching or FSK amplitude modulates $V_C$, which may be sensed using synchronous or, preferably, quadrature detection. One suitable circuit is shown in FIG. 4. The circuit includes a quadrature sine-wave oscillator 400 that may operate at 125 kHz, and which drives the series LC tank circuit comprising an inductor 402 and $C_{th}$ (to which the inductor is coupled electrostatically through the user's body). The output of the tank circuit is applied to a bandpass filter 404, which removes noise and interference, and whose output is itself applied to a pair of voltage multipliers $406_1$, $406_2$. The quadrature and in-phase outputs of oscillator 400 are applied to the other input terminals of multipliers $406_1$, $406_2$, respectively. The outputs of the multipliers, in turn, are applied to a voltage adder 410, whose output—representing the demodulated data—is itself applied to a second bandpass filter 412. A microcontroller 415 (e.g., the PIC16LF84 microcontroller supplied by Microchip Technology Inc., Chandler, Ariz.) receives the data and delivers this to a programmable microcomputer 417, which interprets the data. Microcontroller 415 can disable oscillator 400 in order to facilitate transmission of data to the receiver, e.g., to program the EEPROM through 100% AM modulation of the transmitter signal.

Further details concerning implementation of the quadrature detection circuit may be found in Appendix B of Nivi, *Passive Wearable Electrostatic Tags* (MIT Thesis, September 1997), the disclosure of which is nonessential to the teaching hereof but is incorporated by reference. Other approaches to data encoding (e.g., phase-shift keying, spread spectrum, FM) are also possible.

In an alternative approach, the user's body is employed as a two-way transmission channel, and the worn device actually transmits information (rather than simply modulating detectable electrical characteristics). Most simply, the worn device obtains power from a signal applied to the user's body, the power driving a transmitter circuit that applies a data-containing signal to the user's body for detection by a receiver. Ordinarily, the external device that applies the power signal also reads the data signal; consequently, although different in function and circuitry, the worn and external devices generally both act as transceivers. As used herein, however, the term "transceiver" is intended to broadly connote devices capable of receiving power and/or data, and transmitting power and/or data.

With this approach, it is important to maintain separable power and data signal components. On the other hand, because signals are transmitted directly and not through loading variations, more traditional techniques of signal encoding may be employed.

Figure 5A:
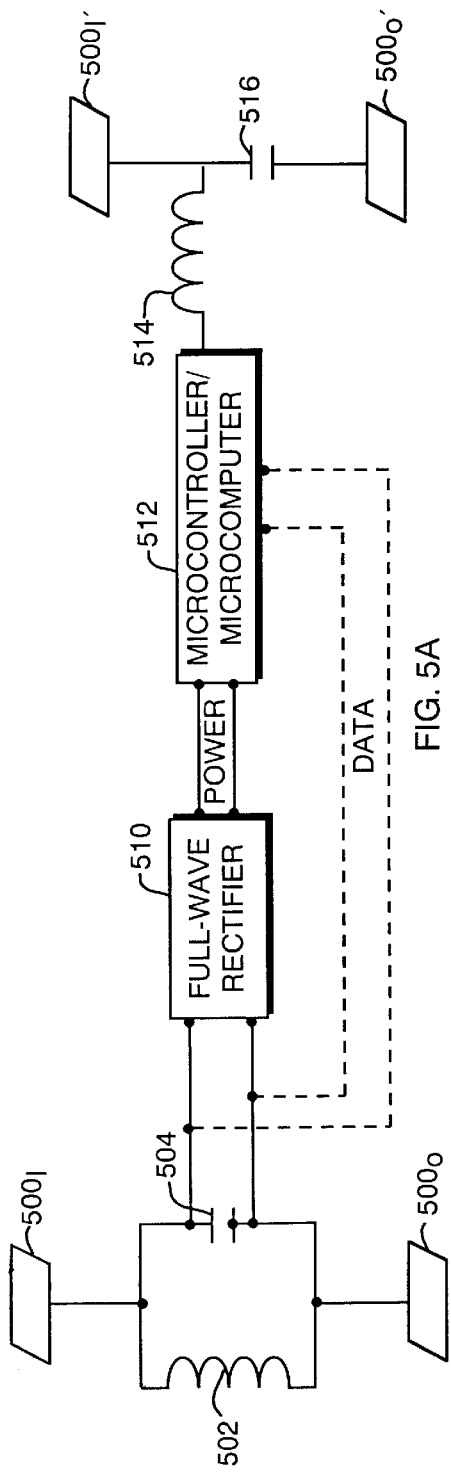
FIGS. 5A and 5B schematically illustrate, respectively, a basic "transmit-mode" relay circuit, and additional circuitry for adapting the relay for two-way communication.

FIG. 5A shows an exemplary transceiver circuit configured for intrabody data transfer, or interaction with an externally located transceiver. In this case, however, data is transmitted directly through signal modulations. As described subsequently, the circuit can be expanded for two-way data exchange, and adapted to other forms of data encoding. The illustrated circuit includes a pair of inner electrodes $500_I$ and $500_{I'}$; and a pair of outer electrodes $500_O$ and $500_{O'}$. Once again, the inner electrodes are generally worn so as to be directly adjacent to or in contact with the user's body, while the outer electrodes are presented to the environment. The electrodes 500 and $500_O$ are connected to a parallel LC tank circuit comprising an inductor 502 and a capacitor 504. The parallel tank circuit acts as a tuned receiver, carrying maximum current when the frequency of the applied power signal matches the resonance frequency of the tank circuit; the high resonance impedance approximates the impedance of the power signal, which is also high due to the small capacitance associated with coupling through the body. In practical operation, power can be transmitted over a fairly wide band of frequencies around the resonant frequency, the size of the band being determined primarily by the Q of the receiver. Of course, maximum power is delivered at when the internal impedances of the transceiver and the power source match.

The received power signal is applied to a full-wave rectifier circuit 510. (Again for optimal power transfer, the impedance of the tank circuit could be matched to that of the rectifier circuit by coupling the rectifier circuit to the tank circuit via an impedance-matching coil, which magnetically couples to inductor 502, rather than by connection across capacitor 504.) A microcontroller or microcomputer 512 receives power from rectifier circuit 510, and applies an output signal to a series LC tank circuit comprising an inductor 514 and a capacitor 516. Electrodes $500_{I'}$ and $500_{O'}$ are connected across capacitor 516. In operation, the device 512—which may be, for example, a PIC 16LF84 chip as discussed above—generates an output signal comprising a pulse train of binary signals, which correspond to a data message. The signals drive the series LC tank circuit, which applies the resulting AC signal to the body via electrodes $500_{I'}$ and $500_{O'}$. The high-low signal transitions corresponding to data bits modulate the frequency of the signal generated by the series tank, producing a "digital FM" (FSK) signal that may be decoded by a receiver. Generally, to minimize system noise and simplify decoding, the power signal differs in frequency from the output frequency band.

Thus, in its most basic realization, the circuit shown in FIG. 5A does no more than receive power and generate data signals that are applied to the body. But by connecting the output of the parallel tank circuit to the data input terminals of device 512 as shown by the dashed lines—that is, the signals received by electrodes $500_I$ and $500_O$ for power but also treating them as received data—the circuit can operate as a full-duplex or half-duplex transceiver. In this configuration, device 512 is programmed to detect and interpret modulations in the incoming signals, which do not affect the constant DC output of rectifier circuit 510 (so that, in effect, power is transmitted through the carrier and data in the signal modulations). Indeed, it is even possible to omit the additional connections to device 512 by configuring rectifier circuit 510 to allow data signals to pass as ripple voltages, and configuring device 512 to detect these voltages.

Device 512 may generate output signals based on received data signals. If a bodyborne array of such circuits are to intercommunicate, full-duplex operation is preferred to ensure a constant supply of power for all of the devices (although the use of a charging capacitor in rectifier circuit 510 permits half-duplex operation if interruptions in the received signal are reliably short enough). For example, if the incoming signal remains unmodulated for more than a threshold duration, device 512 can be programmed to interpret this condition as indicating the absence of transmitted data.

Figure 5B:
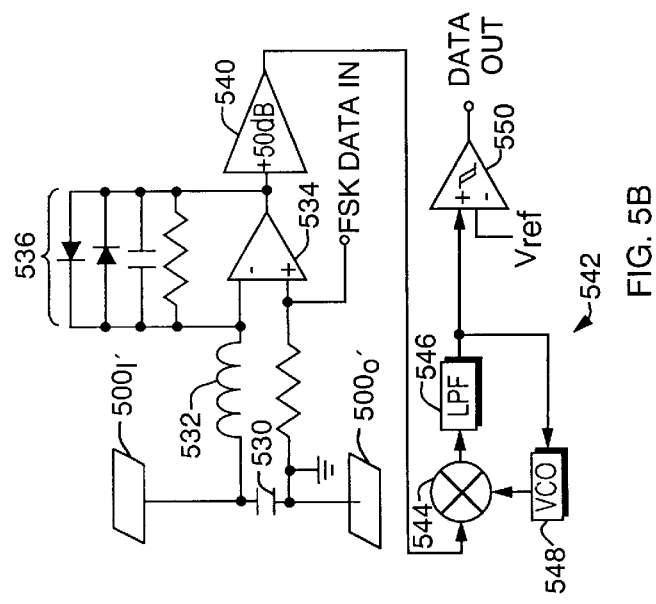

FIG. 5B illustrates another transceiver capable of transmitting both data and power, and which is therefore suited to use as a "reader" that provides power to bodyborne devices with which it interacts. In this circuit, electrodes $500_{I'}$ and $500_{O'}$ are once again connected to a capacitor 530 and an inductor 532 arranged as a series LC circuit, but the inductor is connected to the inverting terminal of an operational amplifier 534, which is itself configured as a buffer by means of a parallel pair of opposed diodes, a capacitor, and a resistor connected across the inverting and output terminals of amplifier 534. One or more gain stages 540 amplify the output of buffer 536, and the amplified signal is fed to an FM detector circuit 542. This circuit is a phase lock loop (PLL) comprising a phase comparator 544, a low-pass filter 546, and a voltage-controlled oscillator (VCO) 548. Finally, the VCO control voltage is applied to the non-inverting terminal of an operational amplifier 550, which exhibits some hysteresis, and is compared to a reference voltage $V_{ref}$ applied to the inverting terminal of amplifier 550.

The circuit shown in FIG. 5B can receive as well as transmit. The series tank circuit consisting of capacitor 530 and inductor 532 preferably has a Q of about 8. When receiving a signal, the series tank serves as a tuned receiver that increases sensitivity to the input frequency band. The buffered, amplified signal entering FM detector circuit 542 causes filter 546 to generate a PLL control voltage, which varies linearly with the input frequency. Comparison of this voltage with $V_{ref}$ by amplifier 550 ensures a binary output, which is applied to the data-input terminal of device 512.

To transmit data, the binary pulse output of device 512 is applied to the non-inverting input terminal of amplifier 534. This causes the voltage at the inverting terminal to follow, thereby applying a signal of variable amplitude to the series LC circuit consisting of capacitor 530 and inductor 532. The signal is transferred to the body of an individual in contact with electrode $500_{I'}$. Although the frequency of the signal remains constant, its amplitude may be modulated. For example, the binary pulse output of device 512 may be transmitted directly via the amplitude modulations. Alternatively, the data may be encoded using FSK. In a preferred implementation, the frequency is shifted from 200 kHz to 250 kHz, so the channel bandwidth is 50 kHz. Other forms of data encoding are of course possible. For example, device 512 can modulate a signal using a pseudorandom code to provide spread-spectrum encoding within a broadband carrier, which supplies also power to the receiving component. Alternatively, the phase rather than the frequency of the carrier signal can be modulated.

The circuit can also function as a loading-mode reader. In this case, a sinusoidal signal is applied by a voltage source to the non-inverting terminal of amplifier 534. The voltage amplitude of the signal at the inverting terminal will change as the frequency of the signal approaches the resonant frequency of a device to which the transceiver is capacitively coupled—that is, the amplitude change will reflect the degree of loading.

Not shown in the figure is a power supply, such as a battery or other voltage source, that supplies power to the various illustrated components. Alternatively, it is also possible to utilize a low-power analog of the illustrated circuit as a bodyborne device that derives power from an applied signal received through a tuned LC circuit, and which is rectified by appropriate circuitry.

It will therefore be seen that the foregoing represents a convenient and flexible approach to interbody and intrabody exchange of information. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of facilitating wireless communication across a user's body, the method comprising:
   a. providing transmission means capacitively coupled to the user and to ground, the transmission means comprising means for detecting variations in an electrical characteristic;
   b. providing receiving means capacitively coupled to the user and to ground, the receiving means exhibiting a detectable electrical characteristic representing information;
   c. operating the transmission means to pass, across the user's body, a time-varying signal having a magnitude sufficient to power the receiving means; and
   d. operating the transmission means to detect the electrical characteristic via capacitive coupling so as to recover the information.

2. The method of claim 1 wherein the detectable electrical characteristic is impedance.

3. The method of claim 1 wherein the detectable electrical characteristic is oscillatory decay of stored energy.

4. The method of claim 1 wherein the detectable characteristic is coupling strength, the coupling strength indicating a distance between the transmission means and the receiving means.

5. The method of claim 1 wherein the detectable characteristic is resonant frequency.

6. The method of claim 5 wherein receiving means comprises an LC circuit having a resonant frequency, the resonant frequency varying in response to an external condition, the transmission means sensing the external condition by locating the resonant frequency.

7. The method of claim 6 wherein the external condition is at least one of (i) temperature, (ii) humidity, (iii) light, and (iv) an applied force.

8. The method of claim 1 further comprising the step of operating the receiving means to vary the detectable electrical characteristic in a manner indicative of information, the transmission means detecting the variations to recover the information.

9. The method of claim 8 wherein the detectable electrical characteristic is impedance, the variations producing, in the transmission means, corresponding variations in loading, the transmission means detecting the impedance variations by means of the loading variations.

10. The method of claim 9 wherein the receiving means comprises an LC circuit having a resonant frequency, the receiving means varying the impedance by shifting the resonant frequency.

11. The method of claim 9 wherein the receiving means comprises an LC circuit having a Q factor, the receiving means varying the impedance by altering the Q factor.

12. Apparatus for wireless communication across a user's body, the apparatus comprising:
   a. transmission means comprising:
      i. a pair of electrodes for capacitively coupling to the user and to ground;
      ii. means for passing, across the user's body via the electrodes, a time-varying signal;
      iii. means comprising means for detecting, via capacitive coupling, variations in a selected electrical characteristic;
   b. receiving means comprising:
      i. a pair of electrodes for capacitively coupling to the user and to ground so as to receive the time-varying signal;
      ii. means for harvesting power from the time-varying signal;
      iii. means for varying an electrical characteristic of the receiver; and
      iv. means for operating the receiving means to vary the electrical characteristic;
   wherein
   c. the time-varying signal has a magnitude sufficient to operate the receiving means; and
   d. the electrical characteristic is varied in a manner indicative of information and detected by the transmission means so as to recover the information.

* * * * *